(12) United States Patent
Brakus

(10) Patent No.: US 6,801,123 B2
(45) Date of Patent: Oct. 5, 2004

(54) ELECTRONIC ORGANIZER AND STORAGE DEVICE

(76) Inventor: Tony George Brakus, Side Door, 814-2nd Ave. N.W., Calgary, Alberta (CA), T2N 0E5

( * ) Notice: Subject to any disclaimer, the term of this patent is extended or adjusted under 35 U.S.C. 154(b) by 72 days.

(21) Appl. No.: 10/197,909

(22) Filed: Jul. 19, 2002

(65) Prior Publication Data
US 2003/0080854 A1 May 1, 2003

Related U.S. Application Data
(60) Provisional application No. 60/325,159, filed on Sep. 28, 2001.

(51) Int. Cl.$^7$ ................................................ G08B 1/00
(52) U.S. Cl. .............................. 340/309.16; 340/309.4; 340/309.7
(58) Field of Search ...................... 340/309.16, 309.3, 340/309.4, 309.7, 309.8, 309.9; 221/2, 3, 15; 368/10, 69, 109

(56) References Cited

U.S. PATENT DOCUMENTS

| | | | | |
|---|---|---|---|---|
| 4,258,354 A | * | 3/1981 | Carmon et al. | 340/309.4 |
| 4,682,299 A | * | 7/1987 | McIntosh et al. | 702/177 |
| 5,289,157 A | * | 2/1994 | Rudick et al. | 340/309.7 |
| 5,720,154 A | * | 2/1998 | Lasher et al. | 53/411 |
| 5,752,235 A | * | 5/1998 | Kehr et al. | 705/3 |
| 6,449,218 B1 | * | 9/2002 | Lluch | 368/10 |

* cited by examiner

Primary Examiner—Van T. Trieu

(57) ABSTRACT

An electronic organizer and storage device has a plurality of compartments for storing tablets or capsules, a plurality of preprogrammed prescription cycles, a compliance verification function unit, a prescription cycle verification unit, a multi-color-multi-function indicator for confirming operation functions, a light for each compartment, and an alarm unit, the light unit and the alarm unit being formed so that a light flashes by the light unit adjacent to a corresponding tablet chamber when tablets or capsules are to be taken and at the same time an audible alarm is activated by the alarm unit so as to provide an audible alarm and at the same time visually identify which tablets or capsules to take next; a unit for storing information on missed alarms; a unit for displaying information on missed alarms using a light means and an audible means; and a unit to queue and transfer information on missed alarms to an external computing device.

13 Claims, 8 Drawing Sheets

FIGURE 1
FIGURE 2
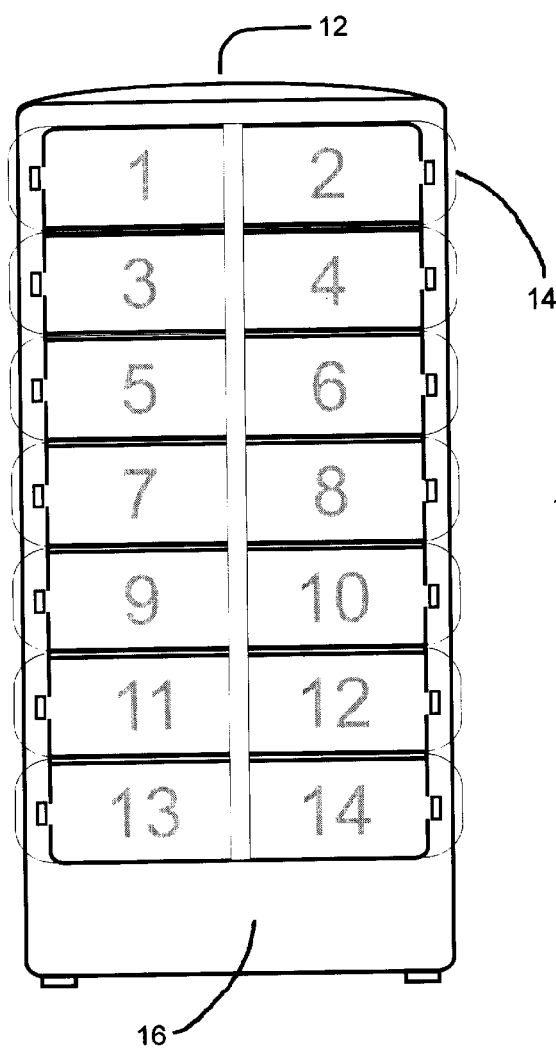
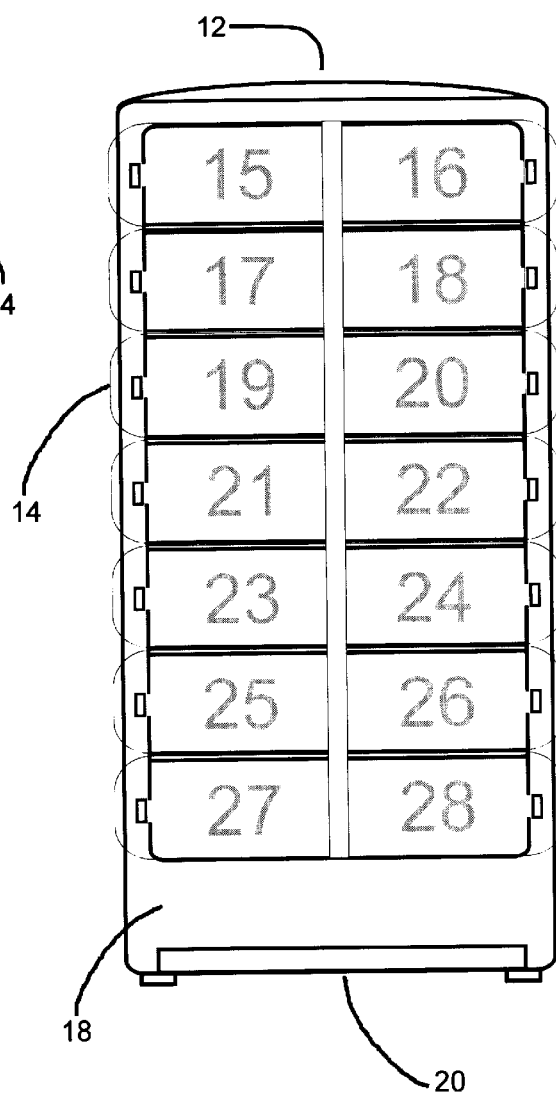

ELECTRONIC ORGANIZER AND STORAGE DEVICE

CROSS REFERENCE TO RELATED APPLICATIONS

This application claims benefit from commonly owned U.S. Provisional Patent Application No. 60/325,159, filed Sep. 28, 2001. The disclosure of this provisional patent application is incorporated herein by reference.

BACKGROUND OF THE INVENTION

The present invention relates to multi-compartment tablet organizers and electronic alarm and storage devices, which organize and store and/or indicate when tablets or capsules should be taken and more specifically to a new electronic organizer and storage device.

The use of tablet organizers and electronic alarm and storage devices, which organize and store and/or indicate when tablets or capsules should be taken, is known in the background art. More specifically, tablet organizers and electronic alarm and storage devices which organize and store and/or indicate when tablets or capsules should be taken heretofore devised and utilized are known to consist basically of familiar, expected and obvious structural configurations, notwithstanding the myriad of designs encompassed by the crowded background art which have been developed for the fulfillment of countless objectives and requirements.

Known background art in tablet organizers include U.S. Pat. No. 5,379,899. Known background art electronic alarm and storage devices include U.S. Pat. No. 6,194,995 BI; U.S. Pat. No. 6,145,697; U.S. Pat. No. 6,119,892; U.S. Pat. No. 6,048,087; U.S. Pat. No. 5,990,782; U.S. Pat. No. 5,838,224; U.S. Pat. No. 5,221,024; and U.S. Pat. No. 4,617,557.

U.S. Pat. No. 5,379,899 discloses a tablet organizer with 28 tablet storage compartments. Tablet compartments are identified and referenced by imprinted lettering and numbers. A pharmacist, health care giver, family member, or the user typically fills this apparatus. Although this apparatus fulfills its objective in providing a better means over prescription vials to organize and store tablets or capsules, it does not incorporate automated reminders of any kind and places the onus of remembering administration times or knowing which tablets or capsules to take, directly on the user, which in most instances is a senior.

The remaining aforementioned patents which do offer enhanced features like audio alarms and programmable timers for remembering when to take tablets or capsules, are typically either too complicated to understand and operate, very limited in the features offered, or too expensive to purchase. While all of the devices known to the background art fulfill their respective, particular objectives and requirements, they do not disclose a new electronic organizer and storage device, which identifies tablets or capsules to be taken by illuminating the respective tablet chamber and sounding an audio alarm simultaneously. Nor do they disclose a new electronic organizer and storage device with a means to store, display, or transfer information on missed alarms.

SUMMARY OF THE INVENTION

It is an object of the present invention to provide a new electronic organizer and storage device, which is easy to understand and operate.

It is another objective of the present invention to provide a new electronic organizer and storage device which provides the user with an enhanced product to assist with the daily administration of tablets or capsules while also providing an efficient evaluation tool for health care givers in assessing a user's ability to self-medicate independently.

It is another objective of the present invention to provide a new electronic organizer and storage device, which will be durable and reliably constructed and can be easily manufactured and marketed.

It is a further objective of the present invention to provide a new electronic organizer and storage device which is susceptible to a low cost of manufacture with regard to both materials and labor, and which accordingly is then susceptible to low prices of sale to the consuming public, thereby making the electronic organizer and storage device economically available at approximately the same retail cost as some multi-compartment tablet organizers which incorporate no enhanced features and well below the retail cost of most electronic alarm and storage devices.

Yet still another objective of the present invention is to provide a new electronic organizer and storage device which provides in the apparatuses and methods of the background art, some of the advantages thereof, while simultaneously overcoming some of the disadvantages normally associated with them such as; ease of use, effectiveness, and affordability.

In these respects, the electronic organizer and storage device which is the subject of the present invention substantially departs from the conventional concepts and designs of the background art, and in so doing provides an apparatus developed to make the taking of daily tablets or capsules easier as well as provide an efficient tool for health care professionals to perform short-term or long-term compliance assessments.

The general purpose of the present invention is to provide a new electronic organizer and storage device apparatus and method which has many advantages over previously mentioned tablet organizers and electronic alarm and storage devices which organize and store and/or indicate when tablets or capsules should be taken and many novel features that result in a new electronic organizer and storage device, which is not anticipated, rendered obvious, suggested, or even implied by any of the background art tablet organizers or electronic alarm and storage devices, either alone or in a combination thereof.

In keeping with these objectives and others which will become apparent hereunder, one feature of the present invention resides, briefly stated, is an electronic organizer and storage device, has means forming a plurality of compartments for storing tablets or capsules; means for providing a plurality of preprogrammed prescription cycles; means for providing a compliance verification function; means for providing a prescription cycle verification; a multi-color multi-function indicator for confirming operation functions; light means provided for each tablet chamber; and alarm means, said light flashes and said alarm means being formed so that a light flashes by said light means adjacent to a corresponding compartment when tablets or capsules are to be taken and at the same time an audible alarm is activated by said alarm means so as to provide an audible alarm and at the same time visually identify which tablets or capsules to take next; means for storing information on missed alarms; means for displaying the stored information using a light means and an audible means for short-term compliance assessments; and means to queue and transfer the stored information to an external computing device for long-term compliance assessments.

The novel features which are considered as characteristic for the present invention are set fourth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF DRAWINGS AND TABLES

FIG. 1 is a front view of the electronic organizer and storage device;

FIG. 2 is a back view of the electronic organizer and storage device;

Figure 3:
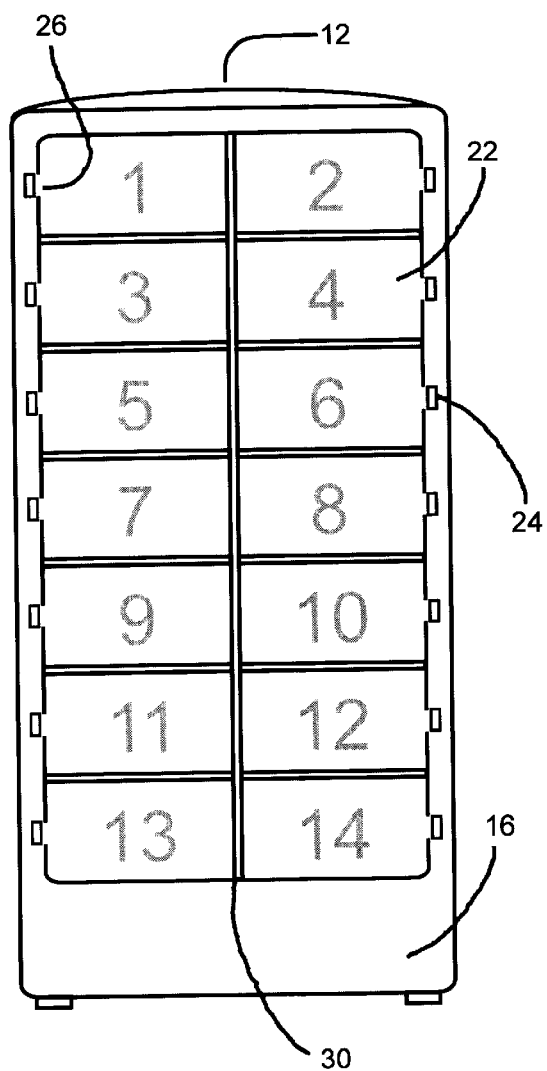
FIG. 3 is a front view of tablet chambers numbered 1 through 14 contained in the front housing.

Table 1 details the alarm spacings in the preprogrammed prescription cycles.

Table 2 details the tri-color indicator's operational colors and functions.

DESCRIPTION OF THE PREFERRED EMBODIMENTS

With reference now to the drawings and tables, and in particular to FIGS. 1 through 11 and Tables 1 and 2, a new electronic organizer and storage device embodying the principles and concepts of the present invention and generally designated by the reference numeral 10, will be described.

Figure 4:
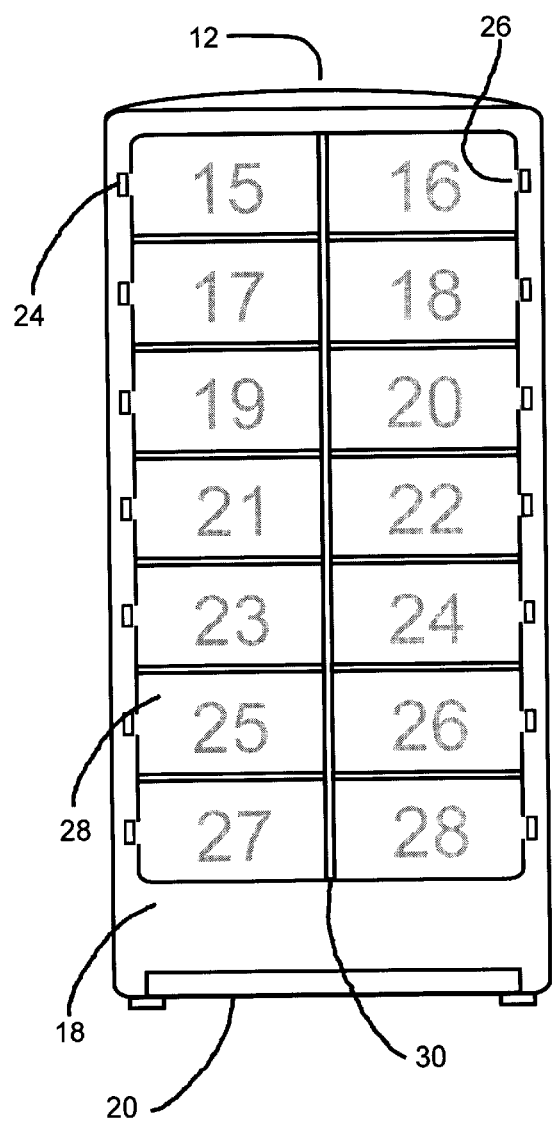
FIG. 4 is a front view of tablet chambers numbered 15 through 28 contained in the back housing.
Figure 7:
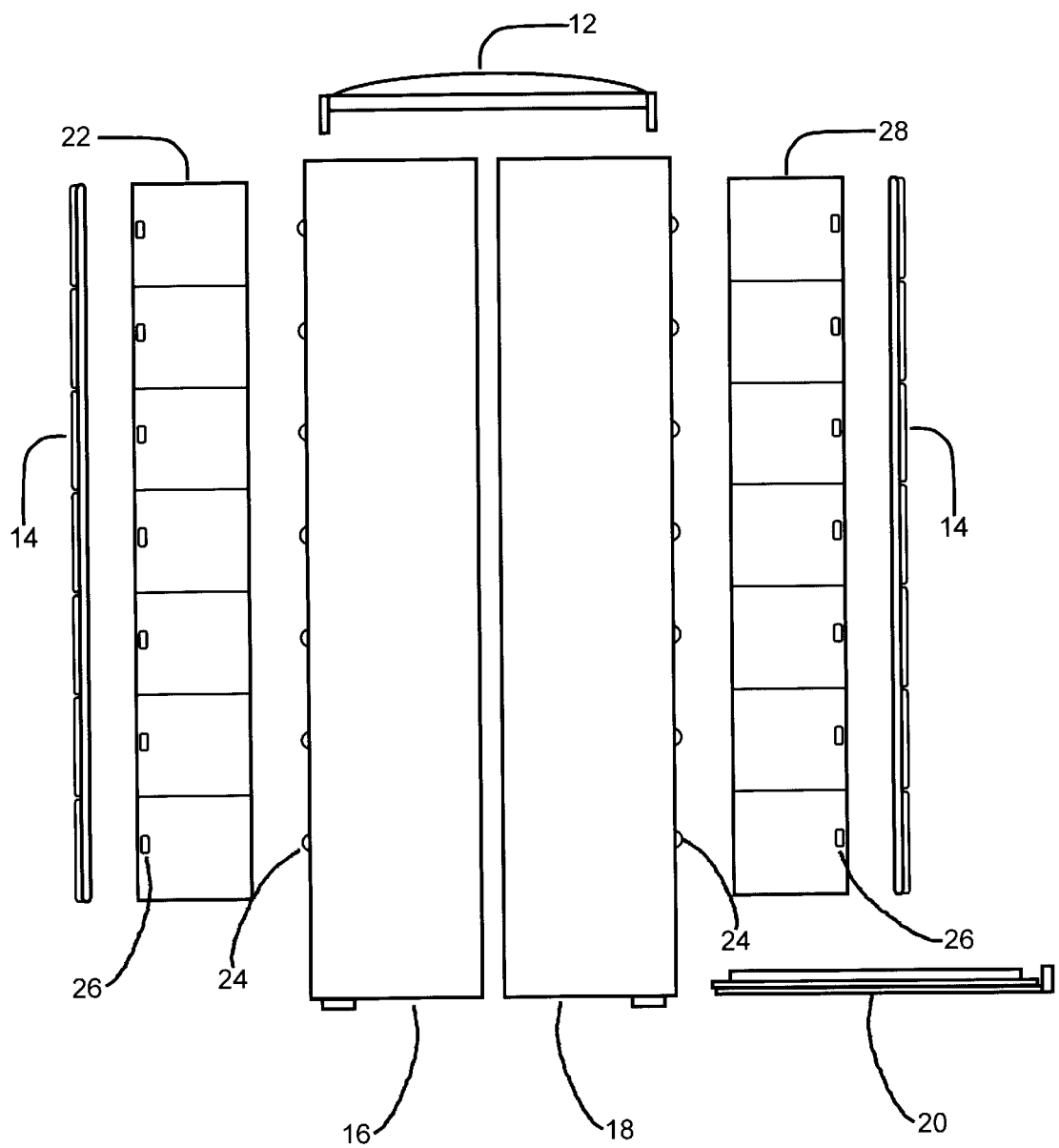
FIG. 7 is an exploded view of the embodiment.
Figure 8:
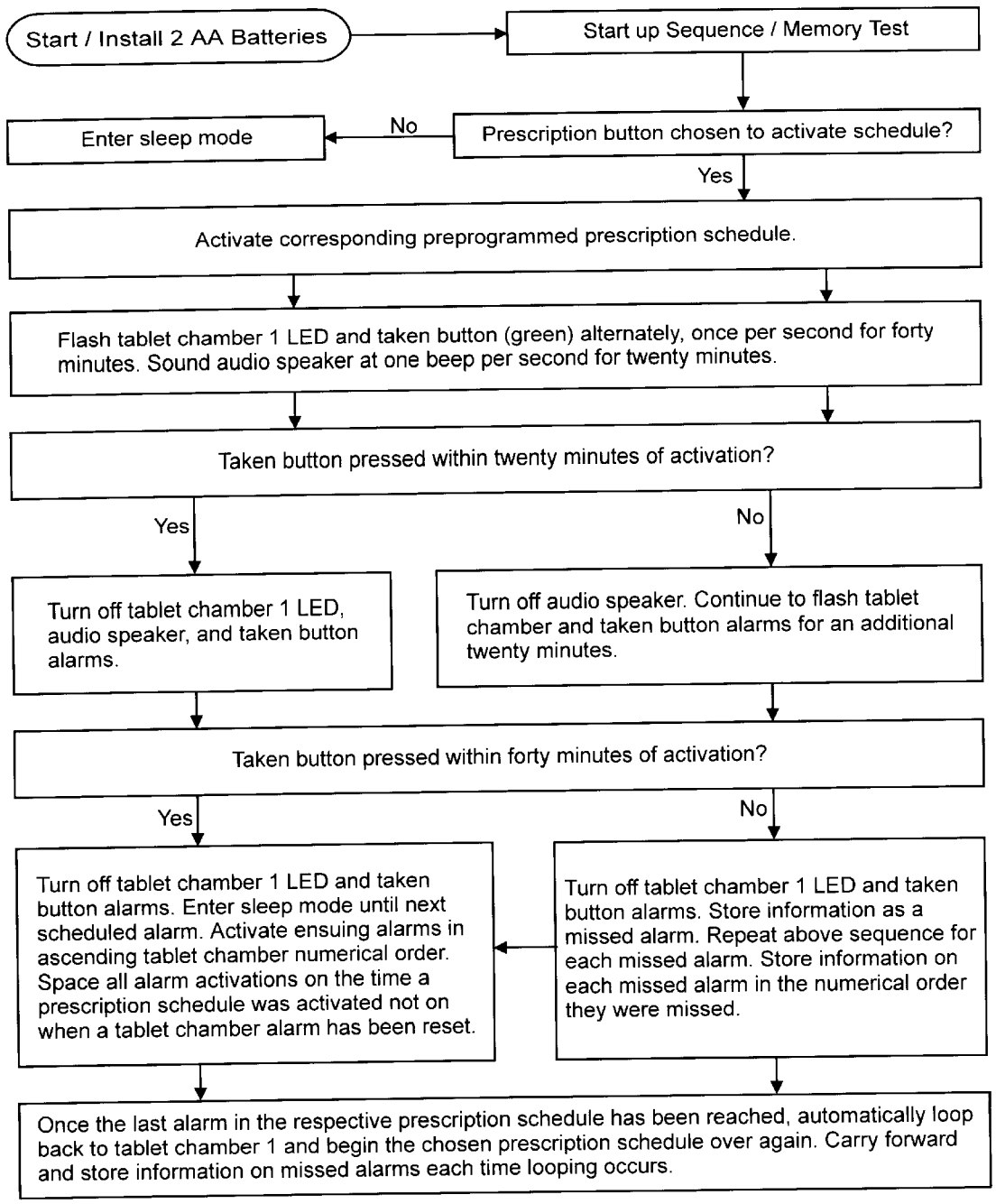
FIG. 8 is a simple block diagram of the primary electronic functions of the electronic organizer and storage device.

In reference to FIGS. 1 & 2, the security lid 12, two translucent door panel assemblies 14, front housing 16, back housing 18, and the bottom compartment lid 20 of the electronic organizer and storage device's 10 are shown. FIGS. 3, 4, & 7 show the two tablet chamber compartment groups 22 and 28. The major structural components of the electronic organizer and storage device 10 consist of three parts molded in an impact resistant polymer, such as polypropylene. Referring to FIGS. 1, 2, & 7, the front and back housings 16 and 18 comprises one injected mold, which snap together over the circuit board 32. The second injected mold piece forms the security lid 12 and the bottom compartment lid 20 as shown in FIGS. 1, 2, 4, 5, & 7. The door assembly units 14 as shown in FIGS. 1, 2, & 7, and the recessed tablet compartments 22 and 28 as shown in FIGS. 1, 2, 3, 4, & 7 form the third injected mould piece.

Light from a visual indicator 24 enters a tablet chamber through small cutouts 26 as shown in FIGS. 3, 4, & 7. The door panel assemblies 14 are translucent to allow the light that is directed into the tablet chambers through the small cutouts 26 to be seen with the door panels in the closed position.

The electronic organizer and storage device 10 typically sits vertically but can also be operated in the horizontal position and the approximate dimensions are 7.5 inches high by 3.5 inches wide by 2.5 inches deep.

FIGS. 3 & 4 shows the numbering sequence of the recessed tablet compartment groups 22 and 28. Fourteen tablet chambers numbered 1 through 14 form tablet compartment group 22 and are fitted into the front housing 16 as shown in FIG. 3. Fourteen tablet chambers numbered 15 through 28 form tablet compartment group 28 and are fitted into the back housing 18 as shown in FIG. 4. Tablet compartments 22 and 28 are filled with tablets or capsules in ascending numerical order beginning with the tablet chamber marked 1. Door panel assemblies 14 and tablet compartments 22 and 28 are removable from the front housing 16 and back housing 18 for filling and cleaning purposes. Tablet compartment groups 22 and 28 can be filled with the tablet compartments inside housings 16 and 18 or by removing them as follows; The door panel assemblies 14 and the tablet compartment groups 22 and 28 are removed from the electronic organizer and storage device 10 by first opening all door panels located on the door panel assemblies 14 and then pulling the door panel assemblies 14 out of the center grooves 30 shown in FIGS. 3 & 4.

Tablet compartment groups 22 and 28 are tolerance fitted into housings 16 and 18 and are removed by pulling them out of the front housing 16 and rear housing 18 using upward pressure. Tablet compartment group 22 is molded to fit only in the front housing 16 and tablet compartment group 28 is molded to fit only in back housing 18. Once the tablet compartment groups 22 and 28 have been filled with tablets or capsules, they are reinstalled by pressing them into their respective housings. The door assemblies 14 are re-installed by lining each assembly up with the center grooves 30 and applying downward pressure. All door panels are then closed by applying downward pressure until they snap into place over the visual indicators 24 and into the tablet chamber compartment groups 22 and 28.

If tablets or capsules are to be taken four times, two times, or once per day, all tablet chambers numbered 1 through 28 are required to be filled. If tablets or capsules are to be taken three times per day, only tablet chambers 1 through 27 are required to be filled. Tablet compartment 28 is left empty.

Figure 5:
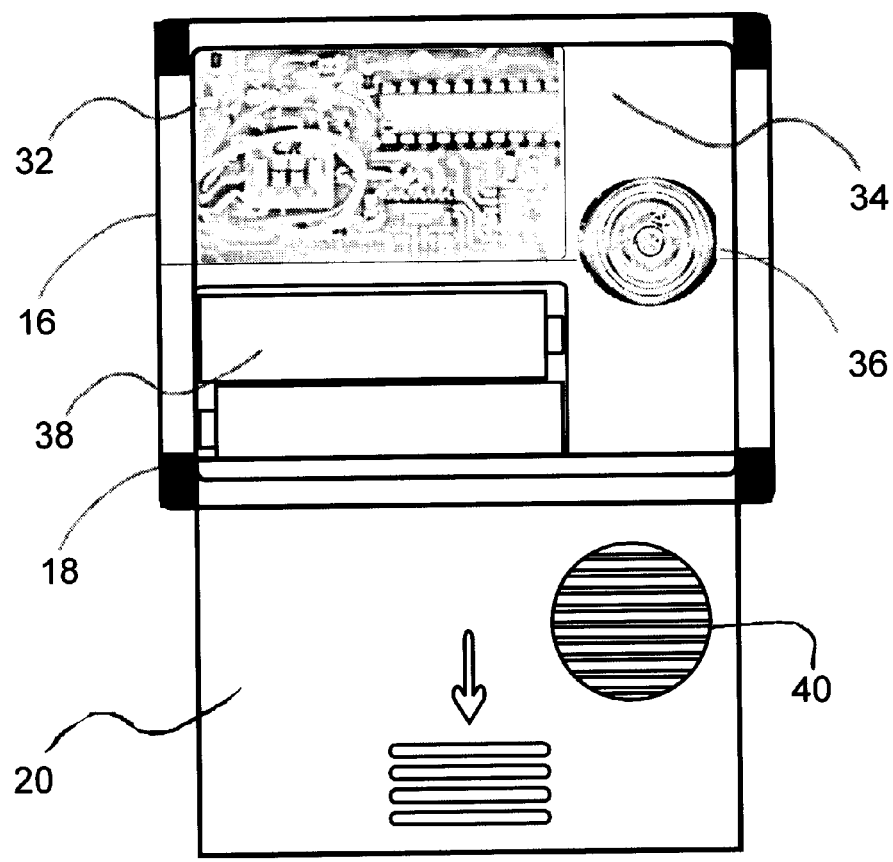
FIG. 5 is a bottom view of the front and back housings, bottom compartment contents, and bottom compartment lid.
Figure 6:
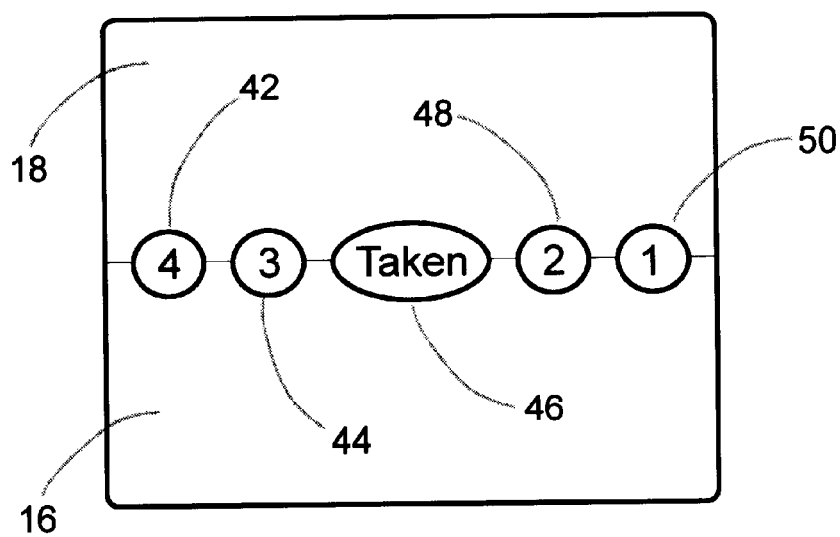
FIG. 6 is a top view of the front and back housings and the five top mounted switches and corresponding user interface buttons.

Two AA batteries 38 are installed by sliding the bottom compartment lid 20 off to access the bottom compartment 34 as shown in FIG. 5. Upon the installation of two AA batteries 38, the circuit board 32 performs a start-up sequence in which all visual indicators 24 illuminate one at a time in tablet chamber ascending numerical order beginning with the tablet chamber marked 1 and ending with the tablet chamber marked 28. This is followed by switch 46 (taken button) as shown in FIG. 6, flashing green five times, accompanied by five simultaneous beeps from the speaker 36 and then stopping. Sound from the speaker 36 is transmitted from the bottom compartment 34 through the bottom compartment lid 20 by means of a speaker grill 40 as shown in FIG. 5. After the start-up sequence is completed, selecting one of the prescription buttons that are associated with switches 42, 44, 48, and 50 as shown in FIG. 6 activates a preprogrammed prescription cycle. The electronic organizer and storage device 10 enters into a sleep mode until a prescription button is selected.

The security lid 12 when installed only allows access to switch 46 (taken button). In order to activate a preprogrammed prescription cycle, the security lid 12 must first be removed to gain access to the prescription buttons and associated switches 42, 44, 48, and 50 as shown in FIG. 6. The security lid 12 is removed by pulling it off of housings 16 and 18 in an upward motion. This exposes switches 42, 44, 48, and 50. These switches are associated with the prescription buttons as follows; Prescription button 4 is associated with switch 42; prescription button 3 is associated with switch 44; prescription button 2 is associated with switch 48; and prescription button 1 is associated with switch 50. The present invention has four prescription cycles, which are preprogrammed and are activated by pressing either switch 42, switch 44, switch 48, or switch 50. The primary function of switches 42, 44, 48, and 50 is to activate a preprogrammed prescription cycle. The number on each prescription button represents how many alarms will activate each day if that button is selected. Table 1 shows the alarm spacings of the preprogrammed prescription cycles in relationship to the alarms per day required.

The initial selection of one of the prescription buttons associated with switches 42, 44, 48, and 50 determines the start time of a preprogrammed prescription cycle. For example, if tablets or capsules are required once per day and it is 8:00 AM when prescription button 1 50 is initially pressed, the preprogrammed prescription cycle which calls for one tablet chamber alarm every 24 hours would be activated.

The tablet chamber marked 1 as shown in FIGS. 1 & 3 would activate upon selection of prescription button 1 50, the tablet chamber marked 2 as shown in FIGS. 1 & 3 would activate at 8:00 AM the following day, and ensuing tablet chamber alarms as shown in FIGS. 1, 2, 3, & 4 would activate in ascending tablet chamber numerical order each day thereafter at 8:00 AM.

The alarm sequence consists of tablet chamber alarms activating in ascending numerical order beginning with the tablet chamber marked 1 and ending with the tablet chamber marked 28 as shown in FIGS. 3 & 4. The only exception to this sequence is if switch 44 (prescription button 3) is chosen to activate a prescription cycle. In this operating mode, the tablet chamber marked 27 as shown in FIG. 4 becomes the last alarm in the alarm sequence.

When the last tablet chamber alarm has been reached in the respective preprogrammed prescription cycle, the alarm sequence loops back to tablet chamber 1 and the chosen preprogrammed prescription cycle begins over again automatically.

The visual indicator 24 assigned to the tablet chamber marked 1, flashes upon the selection of any of the four prescription buttons associated with switches 42, 44, 48, and 50, accompanied by switch 46 (taken button), flashing green once per second and simultaneous beeps at one second intervals from the audio speaker 36. This prompts the user to remove and take the tablets or capsules in the tablet chamber marked 1 and press switch 46 (taken button) to turn off the alarms.

A visual indicator 24 alarm will remain activate unattended in a tablet chamber for forty minutes accompanied by switch 46 (taken button), flashing green at a rate of once per second. The audio speaker 36 sounds simultaneous beeps, at one second intervals, for the first twenty minutes of the alarm only and automatically shuts off to conserve battery strength, if switch 46 (taken button) is not pressed during the first twenty minutes of alarm activation. The visual indicator 24 alarm and switch 46 (taken button), flashing green at a rate of once per second, continue to operate for an additional twenty minutes. If switch 46 (taken button) is not pressed during the total forty-minute alarm, the information on the effected tablet chamber is stored as a missed or late alarm. See FIG. 8.

Figure 9:
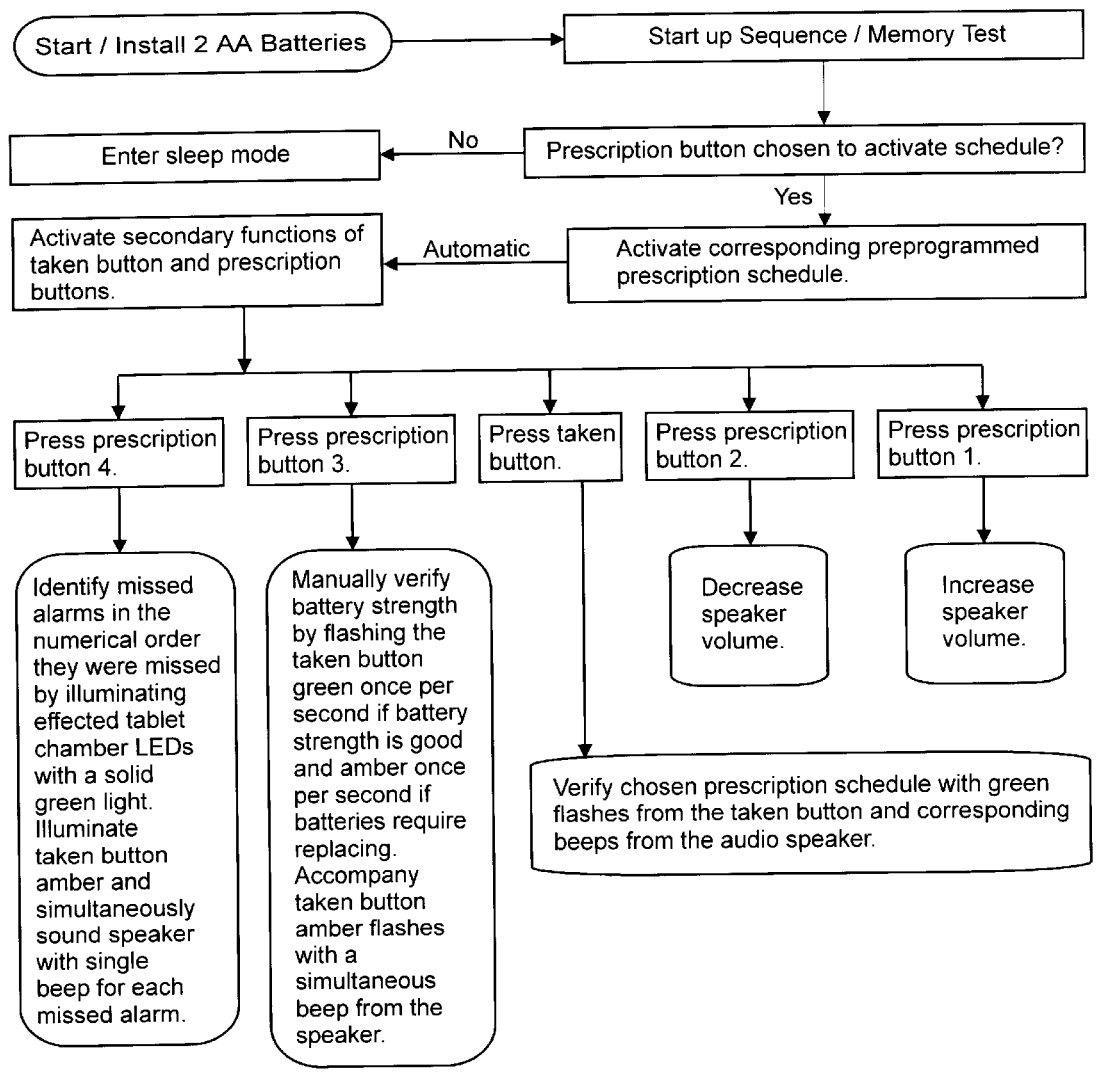
FIG. 9 is a simple block diagram of the secondary electronic functions of the electronic organizer and storage device.

As shown in FIG. 9, once a preprogrammed prescription cycle has been activated, the secondary functions of switches 42, 44, 46, 48, and 50 are automatically initialized. The secondary functions of switches 42, 44, 46, 48, and 50 can only be utilized in-between tablet chamber alarms and perform the following functions when used:

Pressing switch 46 (taken button) verifies the chosen preprogrammed prescription cycle in which the electronic organizer and storage device 10 is operating. This is indicated by the switch 46 (taken button) identifying the chosen preprogrammed prescription cycle in green flashes and sounding simultaneous beeps from the speaker 36. If four green flashes from switch 46 (taken button) are seen and four simultaneous audio beeps from the audio speaker 36 are heard when switch 46 (taken button) is pressed, this verifies that switch 42 (prescription button 4) was initially chosen and that the electronic organizer and storage device 10 is operating in the four alarms per day mode. Three green flashes and three simultaneous beeps would indicate three alarms per day operation. Two green flashes and two simultaneous beeps would indicate two alarms per day operation and one green flash and one simultaneous beep would indicate one alarm per day operation.

Pressing and holding switch 42 (prescription button 4) illuminates individual tablet chambers within tablet compartment groups 22 and 28 one by one with a solid green light from the visual indicator 24 where tablet chamber alarms have not been manually reset using switch 46 (taken button) within forty minutes of activation. Each solid illuminated green light from the visual indicator 24 is accompanied by the switch 46 (taken button) illuminating in a solid amber light and a simultaneous beep from the audio speaker 36 for each missed alarm. Missed or late alarms are visually and audibly identified in the numerical order in which they were missed or late in resetting. Once all missed or late alarms have been identified, the chosen preprogrammed prescription cycle is automatically verified and the electronic organizer and storage device 10 resumes its chosen preprogrammed prescription cycle.

Pressing switch 44 (prescription button 3) manually tests the battery 38 strength and displays the results through switch 46 (taken button) color flashes and beeps from the speaker 36. If switch 46 (taken button) flashes green once per second with no audio sound while switch 44 (prescription button 3) is depressed, the batteries 38 are good. If switch 46 (taken button) flashes amber once per second and is accompanied by a simultaneous beep from the speaker 36 for each amber flash while switch 44 (prescription button 3) is depressed, the batteries 38 should be replaced.

Pressing and holding switch 48 (prescription button 2) decreases the volume from the speaker 36.

Pressing and holding switch 50 (prescription button 1) increases the volume from the speaker 36.

Figure 10:
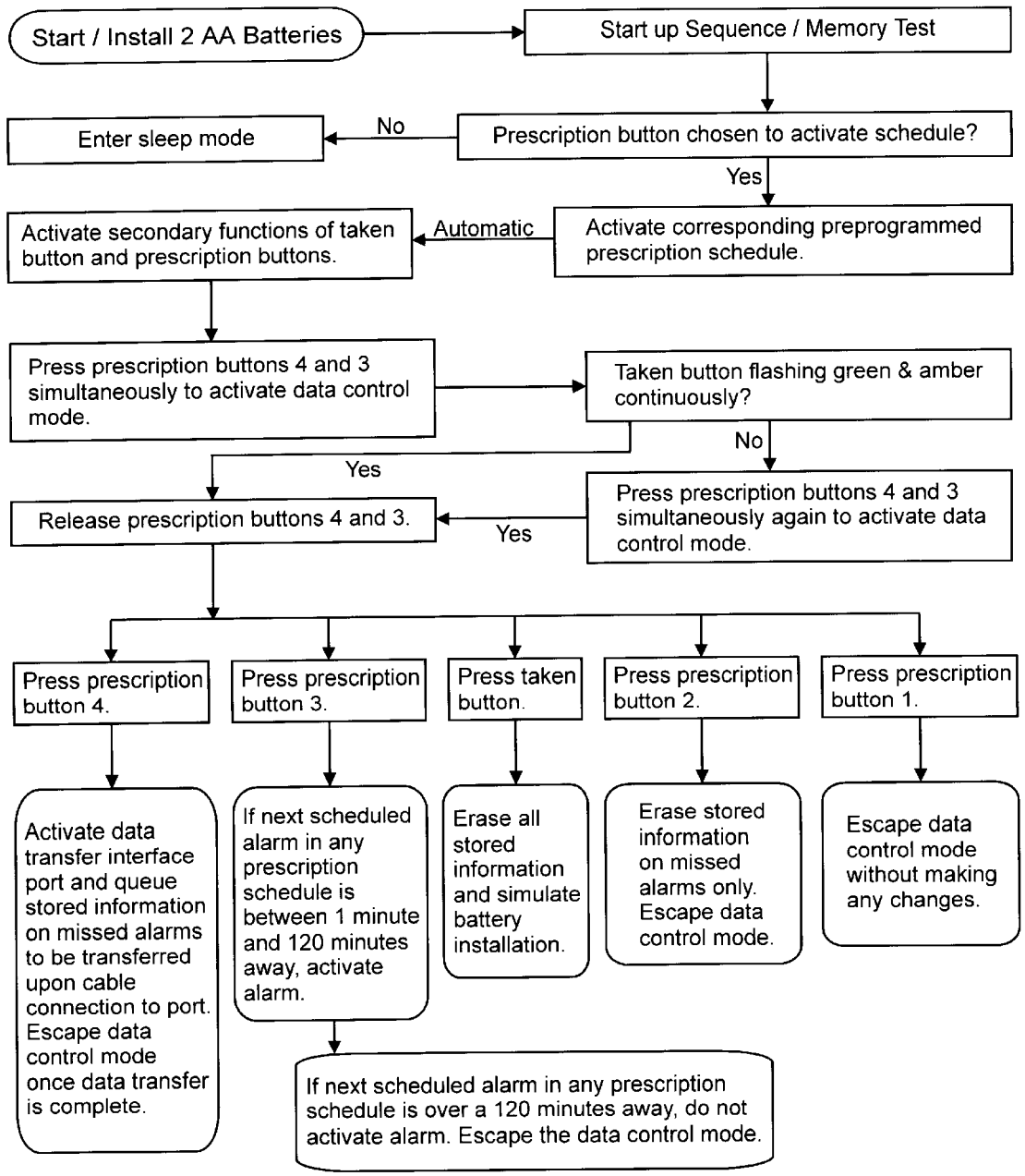
FIG. 10 is a simple block diagram of the data control electronic functions of the electronic organizer and storage device.
Figure 11:
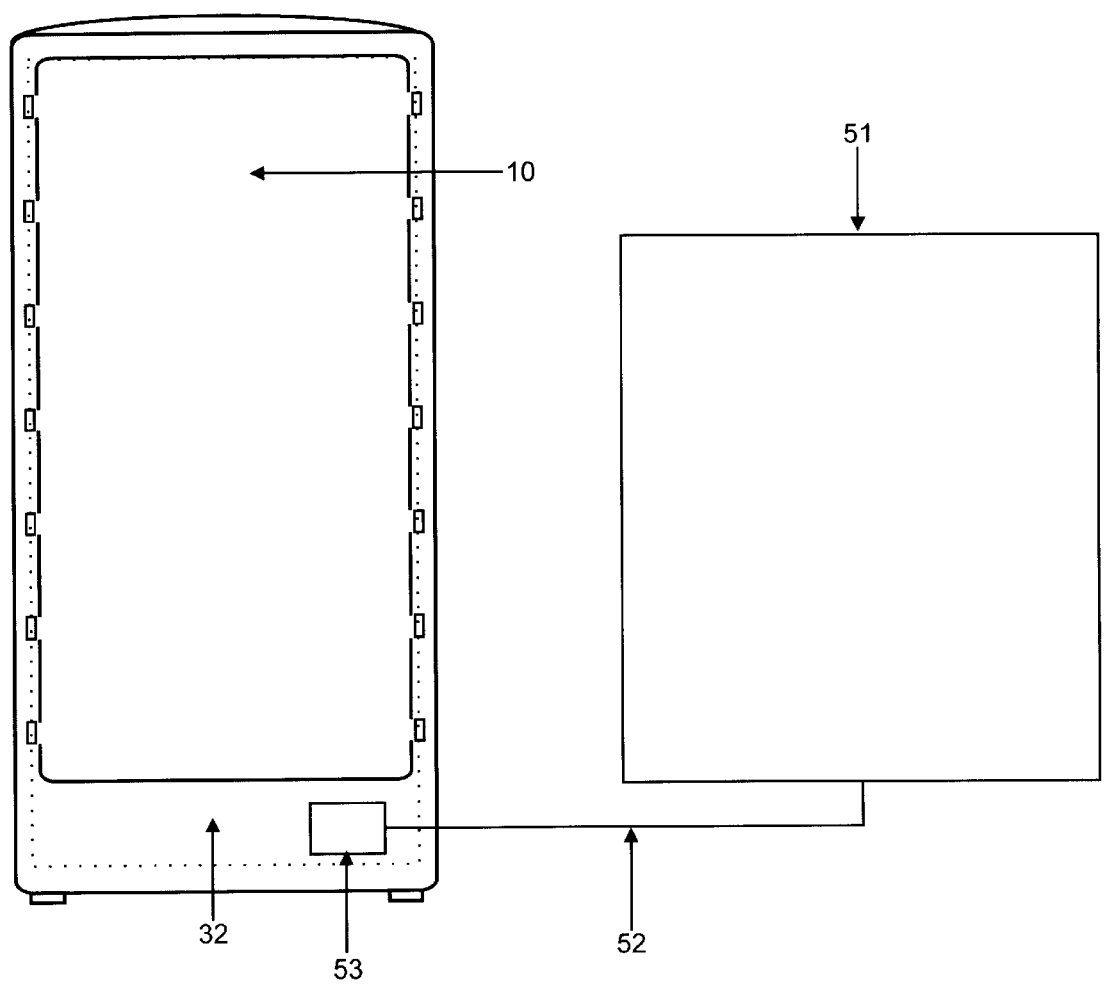
FIG. 11 is a simple block diagram of the data transfer functions of the electronic organizer and storage device.

Pressing switches 42 (prescription button 4) and 44 (prescription button 3) simultaneously with no tablet chamber alarms active, initiates the data control mode as shown in FIG. 10. Once switch 46 (taken button) begins to flash green and amber continuously to confirm that the data control mode has been activated, switches 42 (prescription button 4) and 44 (prescription button 3) are released. In this mode, the data control functions of switches 42, 44, 46, 48, and 50 are initialized and perform the following functions when used:

Pressing switch 42 (prescription button 4) while in the data control mode, activates the data transfer interface port 53 on the circuit board 32 and queues the stored information on missed or late alarms to be transferred to an external computing device 51 upon cable connection 52 to the data transfer interface port 53. Once the data transfer is complete, the chosen preprogrammed prescription cycle is automatically verified and the electronic organizer and storage device 10 resumes its chosen preprogrammed prescription cycle.

Pressing switch 44 (prescription button 3) while in the data control mode activates the next scheduled alarm in any preprogrammed prescription cycle up to two hours earlier. This feature is incorporated to allow a user to take a scheduled dose of tablets or capsules at an earlier time if required.

Pressing switch 46 (taken button) while in the data control mode erases all stored information from the circuit board 32 memory and simulates battery installation and the start-up sequence.

Pressing switch 48 (prescription button 2) while in the data control mode, clears the stored information on missed or late alarms only. All other information on the chosen preprogrammed prescription cycle and next scheduled alarm is kept intact. Once information on missed or late alarms has been erased the chosen preprogrammed prescription cycle is automatically verified and the electronic organizer and storage device 10 resumes its chosen preprogrammed prescription cycle.

Pressing switch 50 (prescription button 1) escapes the data control mode without making any changes. Upon selection of switch 50, the chosen preprogrammed prescription cycle is automatically verified and the electronic organizer and storage device 10 resumes its chosen preprogrammed prescription cycle.

With reference to FIGS. 1 through 10;

Only one visual indicator 24 will flash at any given time.

Individual door panels that comprise the door panel assembly 14 are designed to allow for easy access to tablets or capsules with a hinged design and low resistance snaps.

Preprogrammed alarm cycles activate daily using the time one of the four prescription buttons associated with switches (42, 44, 46, or 50) was initially chosen as the referenced starting point. Late resetting or missing an alarm does not affect the time slot of the next scheduled alarm in any preprogrammed prescription cycle.

With reference to Table 1, this table details the four preprogrammed prescription cycles that activate in relation to the prescription button and associated switch that is chosen. Also shown is each preprogrammed prescription cycle's order of activation in relationship to the tablet chambers they effect; the total time required to complete each alarm sequence before looping occurs; and the refill requirements for tablet compartment groups 22 and 28.

With reference to Table 2, the manual and automatic features of switch 46 (taken button) operational colors, flash rates, and associated functions are detailed. The manual features activate in conjunction with the secondary and data control functions of switches 42, 44, 46, 48, and 50. The automatic features of switch 46 (taken button) include; flashing green once per second in conjunction with each visual indicator 24 at dose times; flashing green once per minute to confirm sufficient battery strength; flashing amber once per minute if battery strength drops below the preset threshold; flashing green three times per minute in-between tablet compartments 21 through 28 or 21 through 27 (3 alarms per day mode) to indicate that tablet compartments will require refilling soon and automatically reverting back to one green flash per minute once alarm sequence looping has occurred; and flashing red sporadically if a fault is detected in the memory of the electronic organizer and storage device 10.

It will be understood that each of the elements described in this disclosure, or two or more together, may also find a useful application in other types of construction differing from the types described above.

While the invention has been illustrated and described as embodied in electronic organizer and storage device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters of Patent is set forth in the appended claims.

TABLE 1

| | | | ALARMS PER DAY | | | |
|---|---|---|---|---|---|---|
| | Alarms | In Tablet Chamber | 4 | 3 | 2 | 1 |
| PRE- | 1st Alarm | 1 | Upon Any Prescription Button Selection | | | |
| PROGRAMMED | 2nd Alarm | 2 | 4 hours later | 7 hours later | 12 hours later | 24 hours later |
| PRE- | 3rd Alarm | 3 | 5 hours later | 7 hours later | 12 hours later | 24 hours later |
| SCRIPTION | 4th Alarm | 4 | 5 hours later | 10 hours later | 12 hours later | 24 hours later |
| CYCLES | 5th Alarm | 5 | 10 hours later | 7 hours later | 12 hours later | 24 hours later |
| | 6th Alarm | 6 | 4 hours later | 7 hours later | 12 hours later | 24 hours later |
| | 7th Alarm | 7 | 5 hours later | 10 hours later | 12 hours later | 24 hours later |
| | 8th Alarm | 8 | 5 hours later | 7 hours later | 12 hours later | 24 hours later |
| | 9th Alarm | 9 | 10 hours later | 7 hours later | 12 hours later | 24 hours later |
| | 10th Alarm | 10 | 4 hours later | 10 hours later | 12 hours later | 24 hours later |
| | 11th Alarm | 11 | 5 hours later | 7 hours later | 12 hours later | 24 hours later |
| | 12th Alarm | 12 | 5 hours later | 7 hours later | 12 hours later | 24 hours later |
| | 13th Alarm | 13 | 10 hours later | 10 hours later | 12 hours later | 24 hours later |

TABLE 1-continued

| | | ALARMS PER DAY | | | |
|---|---|---|---|---|---|
| Alarms | In Tablet Chamber | 4 | 3 | 2 | 1 |
| 14th Alarm | 14 | 4 hours later | 7 hours later | 12 hours later | 24 hours later |
| 15th Alarm | 15 | 5 hours later | 7 hours later | 12 hours later | 24 hours later |
| 16th Alarm | 16 | 5 hours later | 10 hours later | 12 hours later | 24 hours later |
| 17th Alarm | 17 | 10 hours later | 7 hours later | 12 hours later | 24 hours later |
| 18th Alarm | 18 | 4 hours later | 7 hours later | 12 hours later | 24 hours later |
| 19th Alarm | 19 | 5 hours later | 10 hours later | 12 hours later | 24 hours later |
| 20th Alarm | 20 | 5 hours later | 7 hours later | 12 hours later | 24 hours later |
| 21st Alarm | 21 | 10 hours later | 7 hours later | 12 hours later | 24 hours later |
| 22nd Alarm | 22 | 4 hours later | 10 hours later | 12 hours later | 24 hours later |
| 23rd Alarm | 23 | 5 hours later | 7 hours later | 12 hours later | 24 hours later |
| 24th Alarm | 24 | 5 hours later | 7 hours later | 12 hours later | 24 hours later |
| 25th Alarm | 25 | 10 hours later | 10 hours later | 12 hours later | 24 hours later |
| 26th Alarm | 26 | 4 hours later | 7 hours later | 12 hours later | 24 hours later |
| 27th Alarm | 27 | 5 hours later | 7 hours later | 12 hours later | 24 hours later |
| 28th Alarm | 28 | 5 hours later | Not Applicable | 12 hours later | 24 hours later |
| Looping occurs in | | 7 Days | 9 Days | 14 Days | 28 Days |
| Tablet chamber refilling required in | | 7 Days | 9 Days | 14 Days | 28 Days |

TABLE 2

| Color | Activates | Flash Rate | Function |
|---|---|---|---|
| Green | Upon Battery installation | Once per minute | Confirms sufficient battery strength. |
| Green | At each alarm | Once per second | Additional visual aid at dose alarms. |
| Green | By pressing the Taken button | 4, 3, 2, or 1 with speaker | Verifies chosen preprogrammed prescription cycle. |
| Green | In-between the 21st and 27th or 28th alarm | 3 flashes once per minute | Tablet chamber refill indicator. |
| Amber | On low battery level | Once per minute with speaker | Indicates batteries should be replaced. |
| Amber | By pressing prescription button 3 | Once per second with speaker | Indicates batteries should be replaced. |
| Amber | By pressing prescription button 4 | Solid | Additional visual aid to identify missed alarms. |
| Green & Amber | By pressing prescription button 4 & 3 simultaneously | Continuous | Confirms data control mode activation. |
| Red | Upon memory fault detection | Sporadic | Alerts user to discontinue use. |

What is claimed is:

1. An electronic organizer and storage device, comprising means forming a plurality of compartments for storing tablets or capsules; means for providing a plurality of preprogrammed prescription cycles; means for providing a compliance verification function; means for providing a prescription cycle verification function; a multi-color-multi-function indicator for confirming operation functions; light means provided for each compartment; and alarm means, said light means and said alarm means being formed so that a light flashes by said light means adjacent to a corresponding compartment when tablets or capsules are to be taken and at the same time an audible alarm is activated by said alarm means so as to provide an audible alarm and at the same time visually identify which tablets or capsules to take next; and means for storing information on missed alarms; and means for displaying information on missed alarms.

2. An electronic organizer and storage device as defined in claim 1; and further comprising means for queuing and transferring information on missed alarms to an external computing device.

3. An electronic organizer and storage device as defined in claim 2; wherein said light means include an inside light element and an outside light element associated with a corresponding one of said compartments so that simultaneously said inside and said outside of light elements flash when tablets or capsules are to be taken.

4. An electronic organizer and storage device as defined in claim 3; and further comprising low tablet compartment indicating means.

5. An electronic organizer and storage device as defined in claim 2, wherein said queuing and transferring information means is formed as cable means.

6. An electronic organizer and storage device as defined in claim 2, wherein said queuing and transferring information means is formed as wireless means.

7. An electronic organizer and storage device as defined in claim 1; and further comprising compartment means including a plurality of said compartments, a top housing, two translucent door panel assemblies, a front housing, a back housing, a bottom compartment, formed so that said front housing and said back housing form a first element which snaps together over a circuit board, said top housing forms a second element which snaps onto said front housing and back housing, said door assemblies form a third element which is translucent, said bottom compartment lid forms a fourth element, and said compartment units form a fifth element.

8. An electronic organizer and storage device as defined in claim 1; and further comprising a housing; and a plurality of compartment units each having a plurality of said compartments, formed so that said compartments in each of said units are spaced from one another in one direction, while said units are spaced from one another in another direction which is substantially transverse to said one direction, said compartment units being removable from said housing and mountable again on said housing.

9. An electronic organizer and storage device as defined in claim 1; and further comprising means for adjusting an intensity of an audible alarm produced by said alarm means.

10. An electronic organizer and storage device as defined in claim 1; and further comprising means for performing a start-up sequence when said compartments are filled so as to eliminate one compartment at a time; and means for correspondingly flashing a light and producing a sound, so that after the start-up sequence is completed, a sleep mode is entered until a prescription cycle is activated.

11. An electronic organizer and storage device as defined in claim 1; wherein said means for providing preprogrammed prescription cycles is formed so as to provide four different prescription cycles.

12. An electronic organizer and storage device as defined in claim 1; and further comprising battery operated power means; and means for verifying whether said battery means are good or not, said battery verifying means including means for providing a light and means for producing a sound.

13. An electronic organizer and storage device, comprising means forming a plurality of compartments for storing tablets or capsules; means for providing a plurality of preprogrammed prescription cycles; means for providing a compliance verification function; means for providing a prescription cycle verification function; a multi-color-multi-function indicator for confirming operation functions; light means provided for each compartment; and alarm means, said light means and said alarm means being formed so that a light flashes by said light means adjacent to a corresponding compartment when tablets or capsules are to be taken and at the same time an audible alarm is activated by said alarm means so as to provide an audible alarm and at the same time visually identify which tablets or capsules to take next; and means for storing information on missed alarms; and means for displaying information on missed alarms; and means for queuing and transferring information on missed alarms to an external computing device, wherein said light means include an inside light element and an outside light element associated with a corresponding one of said compartments so that simultaneously said inside and said outside of light elements flash when tablets or capsules are to be taken; low tablet compartment indicating means; means for adjusting an intensity of an audible alarm produced by said alarm means; means for performing a start-up sequence when said compartments are filled so as to eliminate one compartment at a time; and means for correspondingly flashing a light and producing a sound, so that after the start-up sequence is completed, a sleep mode is entered until a prescription cycle is activated; said means for providing preprogrammed prescription cycle being formed so as to provide four different prescription cycles; battery operated power means; and means for verifying whether said battery means are good or not, said battery verifying means including means for providing a light and means for producing a sound.

* * * * *